United States Patent [19]
Gordon

[11] Patent Number: 5,236,955
[45] Date of Patent: Aug. 17, 1993

[54] ANTI-FUNGAL AGENT

[75] Inventor: Jeffrey T. Gordon, Olivette, Mo.

[73] Assignee: Washington University, St. Louis, Mo.

[21] Appl. No.: 866,390

[22] Filed: Apr. 10, 1992

[51] Int. Cl.$^5$ .................. A01N 37/00; A01N 37/02; A61K 31/19; A61K 31/22
[52] U.S. Cl. ..................................... 514/557; 514/546
[58] Field of Search ............................... 514/546, 557

[56] References Cited

U.S. PATENT DOCUMENTS 5,073,571 12/1991 Heuckeroth et al. .............. 514/557
5,082,967 1/1992 Heuckeroth et al. .............. 562/512

FOREIGN PATENT DOCUMENTS 327523 8/1989 European Pat. Off. .

OTHER PUBLICATIONS

Gershon et al., J. Pharmaceut. Sci. 68, 86–84 (1979).
Schneirson's Atlas of Diagnostic Microbiol., Abbott Labs., 8th ed. 1982, pp. 48 and 50.
Bryant et al., Proc. Natl. Acad. Sci. USA 86, 8655–8659 (1989).
Bryant et al., Proc. Natl. Acad. Sci. USA 88, 2055–2059 (1991).
Devadas et al, J. Biol. Chem. 267, 7224–7239 (1992).
Johnson et al, Proc. Nat'l Acad. Sci. USA 87, 8511–8515 (1990).

Primary Examiner—Allen J. Robinson
Attorney, Agent, or Firm—Scott J. Meyer

[57] ABSTRACT

A method is disclosed for producing a selective fungicidal effect upon *Cryptococcus neoformans* by treatment of said organism or a mammalian host infected with said organism with a small but effective amount of 4-oxatetradecanoic acid.

2 Claims, 11 Drawing Sheets

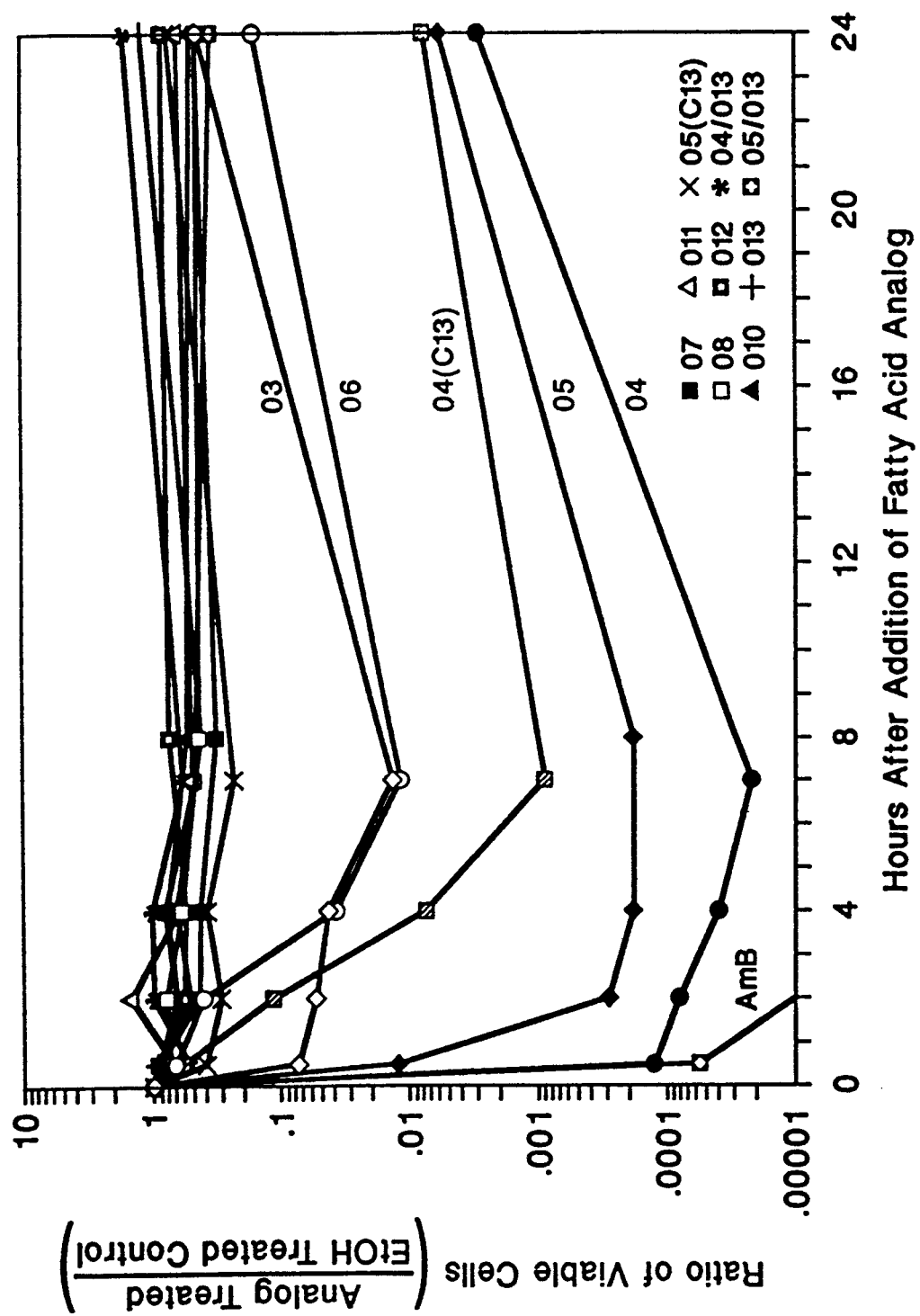

ANTI-FUNGAL AGENT

ACKNOWLEDGEMENT OF SUPPORT

The invention herein was made in part with government support under grants from the National Institutes of Health (A130188 and A127179) and the Monsanto Company. The Federal Government has certain rights in the invention.

BACKGROUND OF THE INVENTION

This invention relates to a method for the control of pathogenic fungi and, more particularly, to the selective fungicidal treatment of *Cryptococcus neoformans* with 4-oxatetradecanoic acid.

*Candida albicans*, a diploid asexual yeast, and *Cryptococcus neoformans*, a heterothallic basidomycete, are major causes of systemic fungal infections in patients with acquired immunodeficiency syndrome (AIDS).

Species of the genus Candida are part of the normal human flora and are the most common yeast pathogens. *Candida albicans*, a dimorphic, asexual yeast, is the most frequently identified pathogen among Candida species. Systemic Candida infections commonly occur in patients who have been immunocompromised by treatment with immunosuppressive medication and broad spectrum antibiotics but are not as frequent in patients with AIDS.

*Cryptococcus neoformans* is the only encapsulated yeast known to be pathogenic in humans. Unlike *C. albicans*, *C. neoformans* is heterothallic, i.e. it has asexual forms with stable mating types. The polysaccharide capsule of *C. neoformans* has an $\alpha$-1,3 mannose backbone with associated glucuronosyl and xylosyl side chains. There are four serotypes of *C. neoformans;* A, B, C and D, each with differing amounts of xylosyl moieties in their capsules. Two varieties are recognized: *C. neoformans var. neoformans* (serotypes A and D) and *C. neoformans var. gatti* (serotypes B and C). The capsule is one of the factors that determines the virulence of *C. neoformans*. Infection occurs via inhalation of aerolized spores. Depending on the infecting dose and immunologic status of the patient, chronic systemic infection can occur affecting the lung, skin or meninges. In immunocompromised patients, such as those with AIDS, cryptococcosis has a more malignant course, frequently presenting with bizarre cutaneous manifestations and spreading to the central nervous system where it is often refractory to treatment.

At the present time, therapy for systemic *C. albicans* and *C. neoformans* infections is less than ideal. Patients are currently treated with amphotericin B alone or in combination with the nucleoside analog 5-fluorocytosine. Alternatively, lanosterol 14$\alpha$-demethylase inhibitors such as the imidizaole ketoconazole or the triazole fluconazole are used. Cryptococcosis in AIDS patients, unlike in immunocompetent hosts, is frequently resistant to treatment with amphotericin B and 5-fluorocytosine. Moreover, while amphotericin B is the only fungicidal agent available, it is nephrotoxic, does not penetrate into the cerebrospinal fluid, and must be given intravenously. Ketoconazole and the newer azoles are fungistatic rather than fungicidal. These problems are particularly important in patients with AIDS: 40–50% fail primary therapy and no therapy currently available is curative.

Gershon et al., *J. Pharmaceut. Sci.* 68, 82–84 (1979), synthesized a series of n-alkoxyacetic acids (ROCH$_2$COOH) where n=C1–C9, C11 or C13, and tested their effects on the growth of a variety of fungal species, including *C. albicans*, in Sabouraud dextrose agar. While 3-oxaundecanoic acid had the broadest spectrum and highest potency, several other compounds, including 3-oxatetradecanoic acid, inhibited growth. The mechanism(s) that are responsible for these anti-fungal effects were not defined.

$C_{13}$–$C_{14}$ Fatty acid analogs in which a methylene group normally in carbon position from 4 to 13 is replaced with oxygen are disclosed as useful antiviral agents, e.g. retroviruses such as HIV-1, in U.S. Pat. No. 5,073,571. In particular, 13-oxatetradecanoic acid, which is a substrate for human acyl CoA synthetase and human myristoylCoA:protein N-myristoyltransferase (NMT), inhibits HIV-1 replication in acutely and chronically infected human T-lymphocyte cell lines at doses which do not cause cellular toxicity. See, e.g., Bryant et al., *Proc. Natl. Acad. Sci. USA* 86, 8655–8659 (1989); Bryant et al., *Ibid* 88, 2055–2059 (1991); Devadas et al., *J. Biol. Chem.* 267, 7224–7239 (1992). Studies with tritiated 13-oxatetradecanoic acid indicate that this fatty acid analog is incorporated into HIV-1 Pr55$^{gag}$ and nef and some but not all cellular proteins. See, Johnson et al., *Proc. Natl. Acad. Sci.* 87, 8511–8515 (1990); Bryant et al., Ibid. 88, 2055–2059 (1991).

BRIEF DESCRIPTION OF THE INVENTION

In accordance with the present invention, a method is provided for producing a selective fungicidal effect upon *Cryptococcus neoformans* by treatment of said organism or a mammalian host infected with said organism with a small but effective amount of 4-oxatetradecanoic acid, $CH_3(CH_2)_9O(CH_2)_2COOH$, or its $C_1$–$C_4$ alkyl esters.

Surprisingly, 4-oxatetradecanoic acid has markedly different effects upon *C. neoformans* and *C. albicans*. Metabolic labeling studies using [$^3$H]myristate reveal that both of these organisms synthesize a small number of N-myristoylproteins. Despite the fact that the two organisms appear to incorporate the radiolabeled 4-oxatetradecanoic acid to a comparable extent into their small number of cellular N-myristoylproteins, that fatty acid analog unexpectedly is a considerably more effective fungicide or fungistatic agent against *C. neoformans* than it is against *C. albicans*.

The selective fungicidal effect of the 4-oxatetradecanoic acid is further surprising in that movement of the site of oxygen substitution of one methylene group towards either the carboxyl, e.g. as in 3-oxatetradecanoic acid, or the omega terminus, e.g. as in 5-oxatetradecanoic acid, dramatically reduces these effects on growth and viability of *C. neoformans*.

Effective antifungal activity against cell cultures of *Cryptococcus neoformans* is obtained by treatment with from about 100 to 300 $\mu$M concentrations of 4-oxatetradecanoic acid.

Metabolic labeling studies confirm that 4-oxatetradecanoic acid is a substrate for *C. neoformans* NMT. Since 4-oxatetradecanoic acid also inhibits HIV-1 replication in an acutely infected human T lymphocyte cell line, it is believed that (i) *C. neoformans* NMT and/or its substrates may be an attractive target for anti-fungal therapy and (ii) that acylCoAs, which have altered physical-chemical properties relative to myristoylCoA, may potentially inhibit both HIV-1 replication in vivo as well as the growth of organisms that cause opportunistic infections in patients with AIDS.

DETAILED DESCRIPTION OF THE INVENTION

While the specification concludes with claims particularly pointing out and distinctly claiming the subject matter regarded as forming the present invention, it is believed that the invention will be better understood from the following detailed description taken in conjunction with the accompanying drawings.

For convenience, the series of oxatetradecanoic acids, from 3-oxatetradecanoic acid to 13-oxatetradecanoic acid, are also referred to herein by the shorthand nomenclature, O3 to O13, respectively.

Figure 1A:
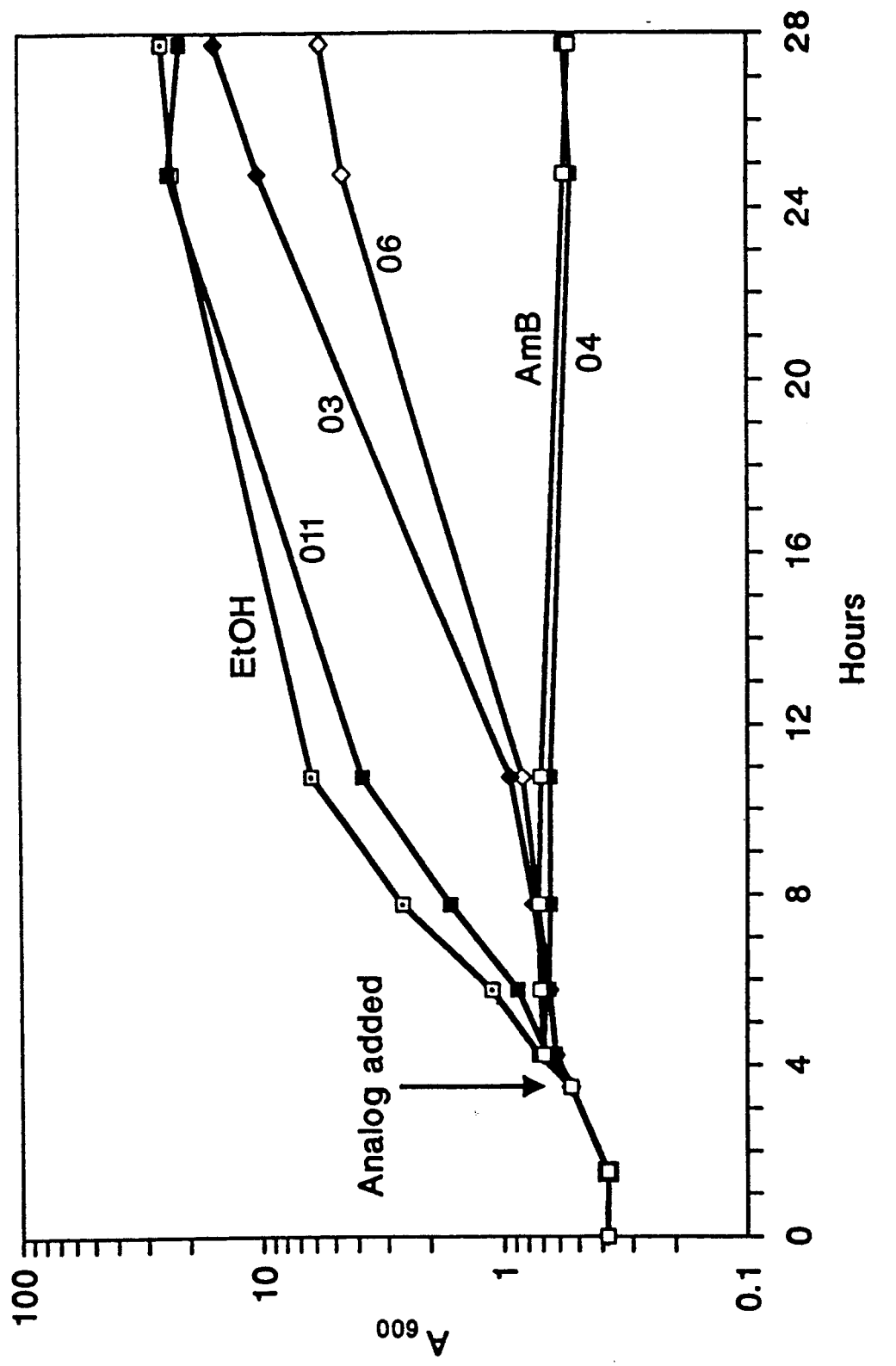
Figure 1C:
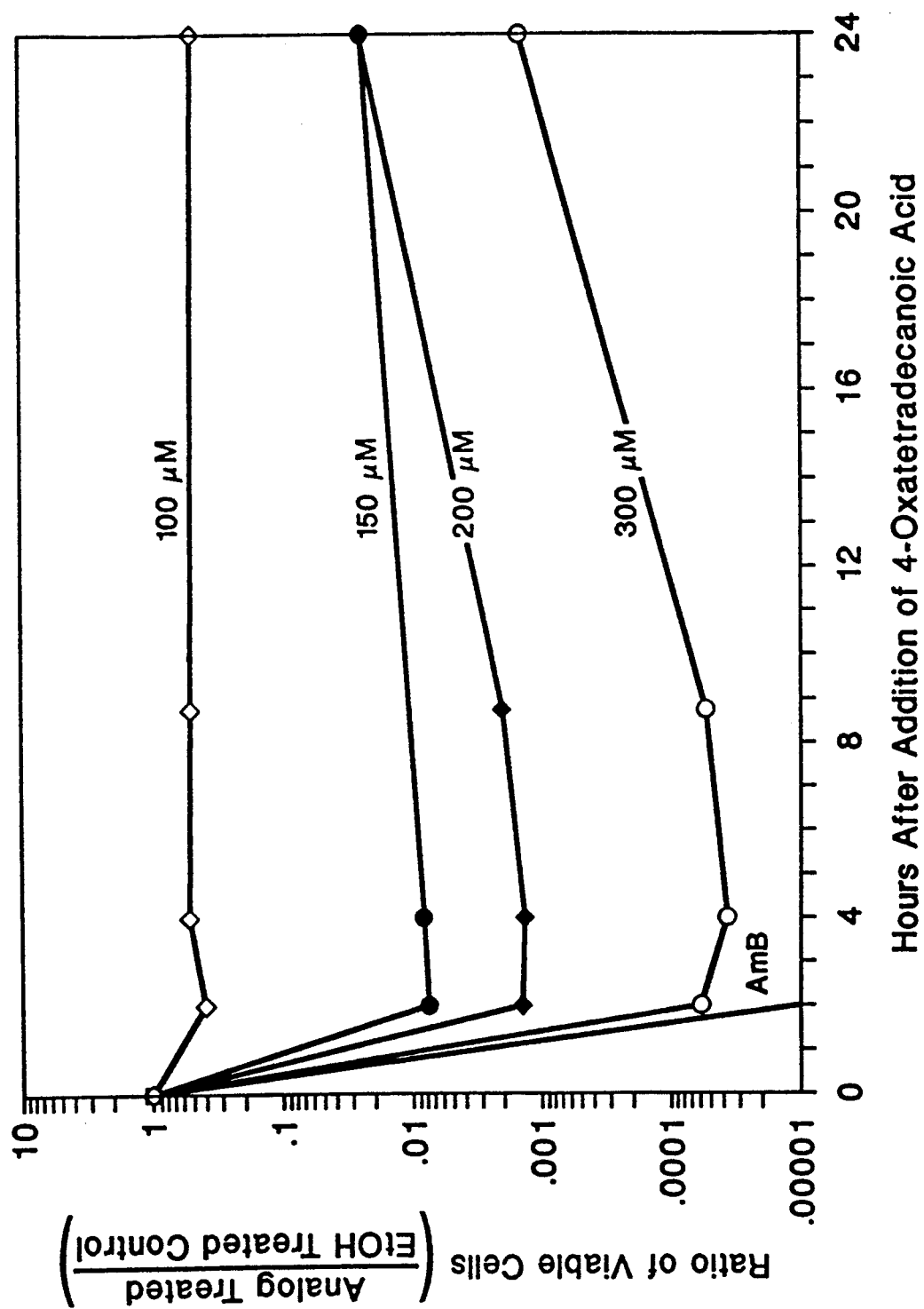

FIG. 1 shows in three panels, FIG. 1A, FIG. 1B, and FIG. 1C, the effect of oxatetradecanoic acids on the growth of C. neoformans. Panel A, survey of the effects of several oxatetradecanoic acids on the growth of C. neoformans. A culture of C. neoformans was grown at 30° C. in SAB media to midlog phase ($A_{600} \sim 0.5$). A single dose of fatty acid was then added to subcultures (final concentration = 300 µM). EtOH(0.1%) was used as a negative control. Amphotericin B (AmB) was added (final concentraton = 55 µM) as a positive control. Aliquots were withdrawn from the subcultures 0, 0.5, 2, 4, 7, 21, and 24 h after these additions and then absorbance at 600 nm was measured. All assays were done in duplicate or triplicate. A representative test is shown. Panel B, survey of the effects of oxatetradecanoic acids, dioxatetradecanoic acids and oxatridecanoic acids on the viability of C. neoformans. Fatty acid analog was added to the cultures as in Panel A. Aliquots were withdrawn 0.5, 2, 4, 7 or 8, and 24 h later and plated on SAB-agar at various dilutions to determine the number of viable organisms/ml culture. All assays were done in duplicate. Data from a representative test are expressed as the ratio of viable cells in treated cultures relative to a control culture that received 0.1% EtOH. A positive control culture received a single dose of amphotericin B (55 µM); Panel C, dose-dependent reduction in the viability of C. neoformans after addition of 4-oxatetradecanoic acid (O4) to cultures during log-phase growth at 30° C. in SAB. A single dose of the analog was given at T=0 h in the amount indicated and aliquots of the culture were withdrawn at various times to determine the number of viable cells. All assays were done in triplicate. A representative test is shown.

Figure 2:
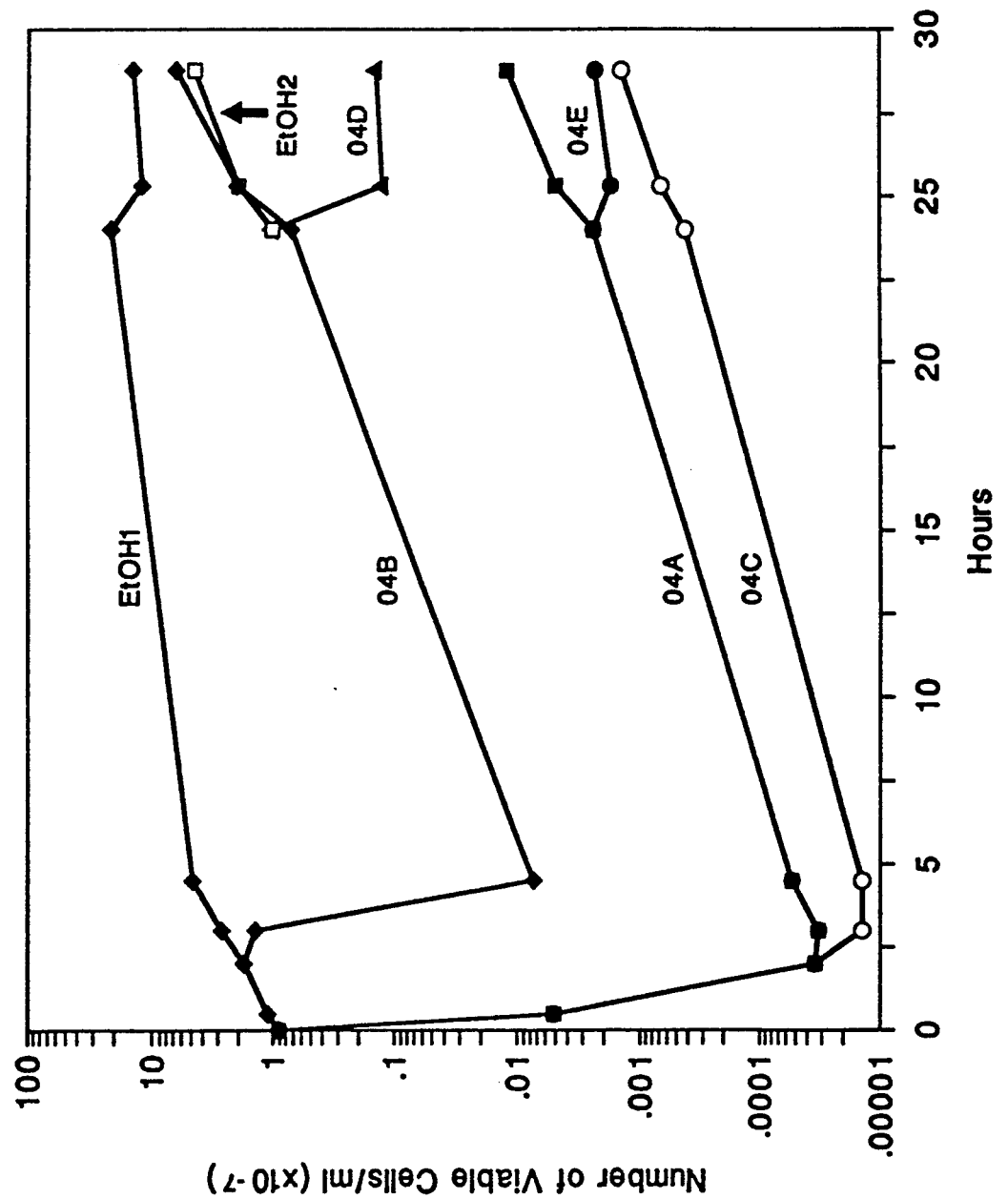

FIG. 2 shows an assessment of the metabolic stability of 4-oxatetradecanoic acid in C. neoformans cultures. Cultreus of C. neoformans were exposed to a single dose of 300 µM O4 or 0.1% EtOH during mid-log phase growth (O4A, EtOH1) as in FIG. 1. Two hours later, an aliquot was removed from the culture and subjected to centrifugation at 1500×g for 10 min. The "used" O4-containing media was added to EtOH-treated cells (O4B). "Fresh" O4 was added to cells (final concentration = 300 µM) that had already been exposed to O4 for 2 h (O4C). at 24 H, O4-treated cells were again pelleted and resuspended in "fresh" O4-containing media (final concentration = 300 µM (O4E)). The "used" O4 media was added to a fresh culture of untreated cells (O4D) and their growth was compared to an identical population of cells treated with EtOH alone (EtOH2).

FIG. 3 shows in four panels, FIG. 3A, FIG. 3B, FIG. 3C and FIG. 3D, the effect of selected oxatettadecanoic acids on the viability of S. cerevisiae and C. albicans. Oxatetradecanoic acids were added (final concentraton = 25–500 µM) as a single dose to log phase cultures of C. alibcans grown in SAB at 30° C. (Panels A and B) and to log phase cultures of S. cerevisiae grown in YPD at 30° C. (Panels C and D). The results were compared to the number of viable organisms present in cultures treated with 0.1% EtOH alone. As with C. neoformans, control tests indicated that this concentration of EtOH did not affect the growth of the organisms. A single does of alphotericin B (final concentration = 55 µM) was added to parallel cultures which served as positive controls. Assays were done in duplicate. Representative tests are shown.

Figure 4:
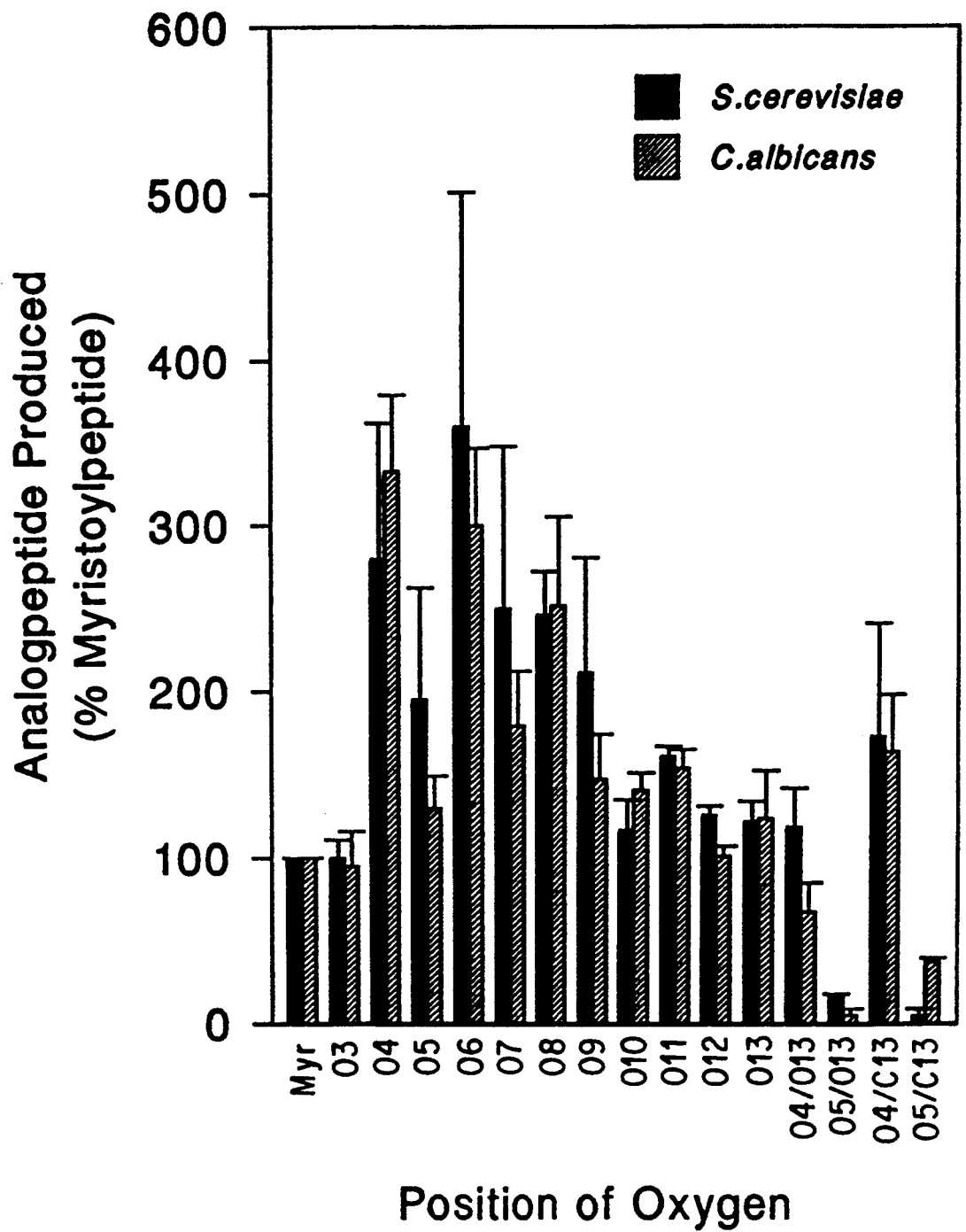

FIG. 4 shows the substrate properties of oxatetradecanoylCoAs for S. cerevisiae and C. albicans NMTs. Details of the single point, discontinuous, in vitro NMT assay are described in Examples, below. A tritiated octapeptide derived from residues 2–9 of HIV-tritiated octapeptide derived from residues 2–9 of HIV-I Pr55$^{gag}$ (GARA[$^3$H]SVLS-NH$_2$) was used in all assays. The amount of analogpeptide produced is expressed as a percentage of myristoylpeptide generated in a control incubation. All assays were performed in triplicate. The mean ±1 standard deviation is shown. Under the assay conditions employed, the amount of myristoylpeptide generated by purified E. coli-derived S. cerevisiae NMT ranged from $5\times10^5$ to $2\times10^6$ pmol/mg enzyme/min while the amount of myristolypeptide produced by purified E. coli-derived, C. albicans NMT ranged from $4\times10^5$ to $1.5\times10^6$ pmol/mg enzyme/mni.

Figures 5A, 5B, 5C:
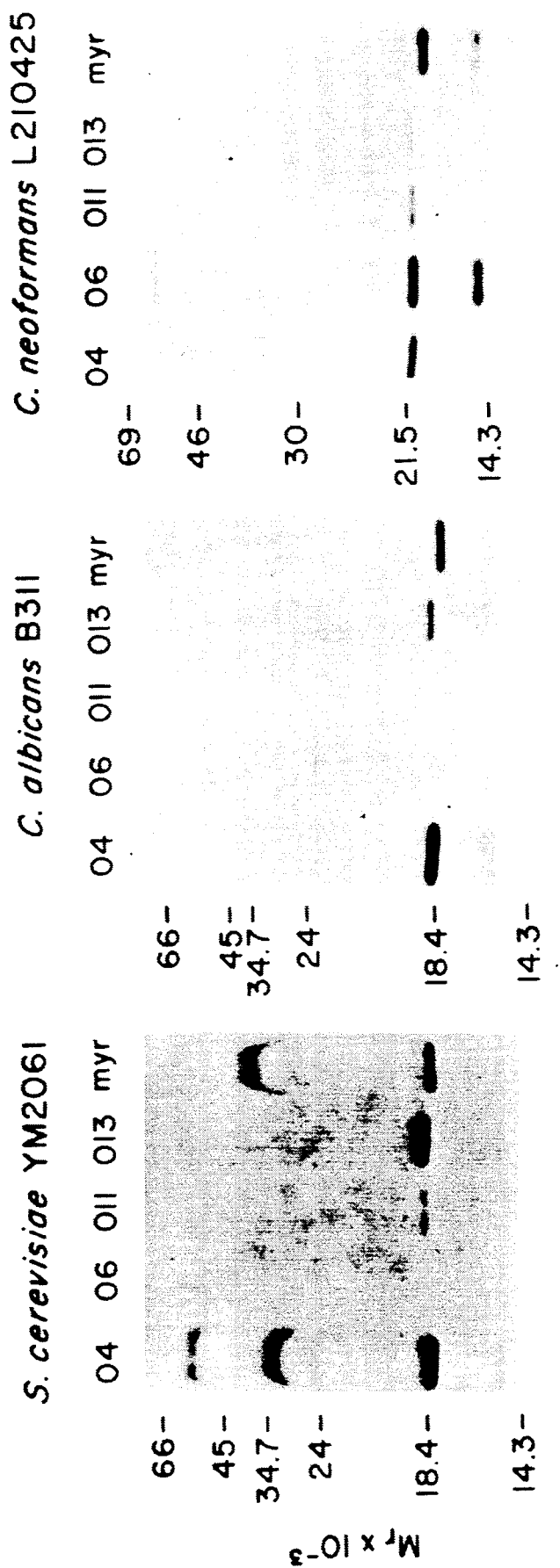

FIG. 5 shows in three panels, FIG. 5A, FIG. 5B and FIG. 5C, an analysis of the incorporation of exogenous [$^3$H]myristate, 4-oxa-, 6-oxa-, 11-oxa- and 13-oxatetradecanoic acids into the N-myristoylproteins produced by S. cerevisiae (FIG. 5A), C. albicans (FIG. 5B), and C. neoformans (FIG. 5C) during exponential growth at 30° C. Cells were labeled for 1 h with fatty acids of equal specific activity. Total cellular proteins were reduced, denatured and subjected to SDS-PAGE. Gels were treated overnight with 1 N hydrocylamine (pH 10) at room temperature followed by EN$^3$HANCE. Fluorography was performed at −80° C. The exposure time for all gels was identical (2 weeks) as was the total amount of cellular protein added to each lane (100 µg).

Figure 6:
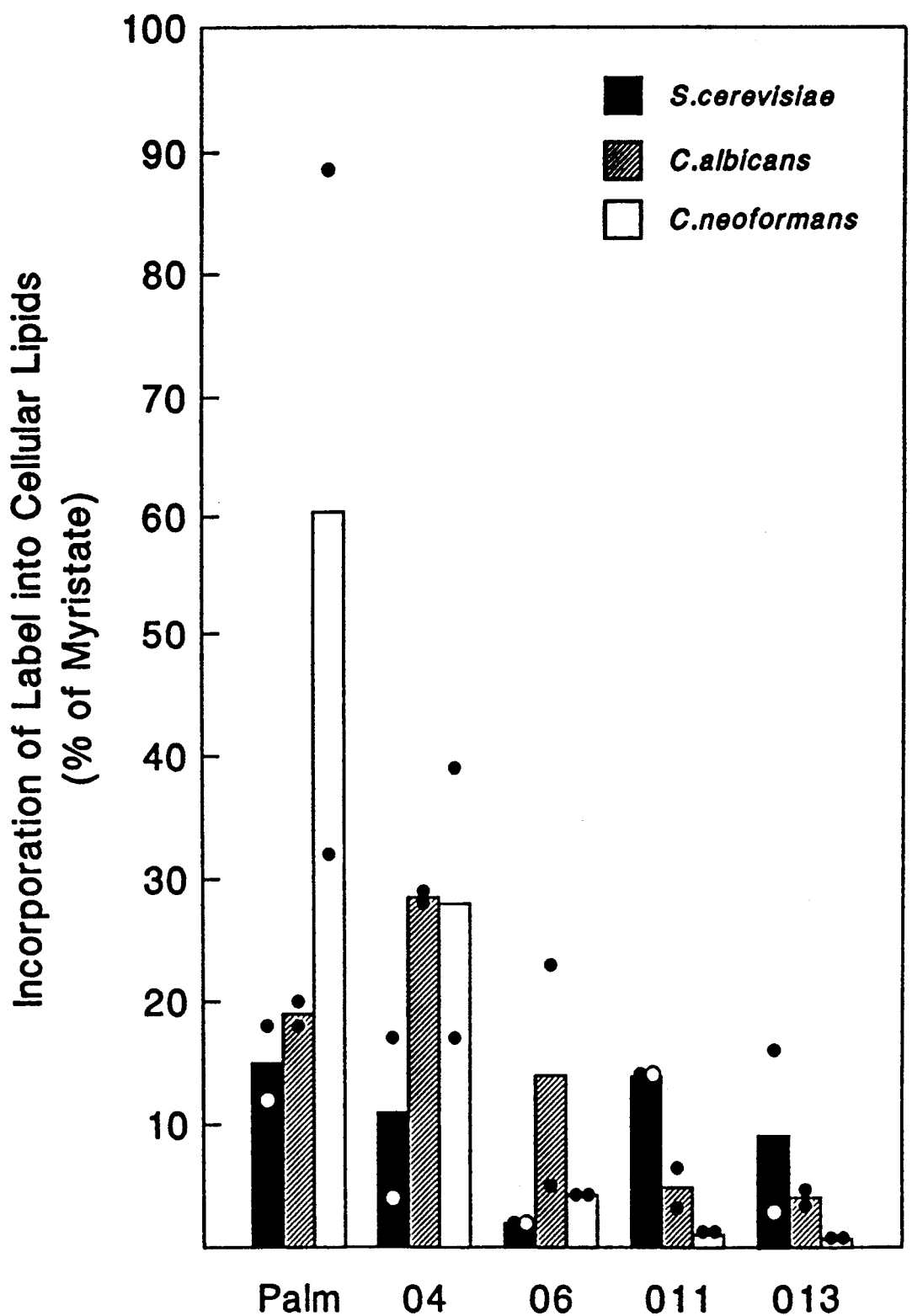

FIG. 6 shows the incorporation of [$^3$H]myristate, palmitate, and oxatetradecanoic acids into total cellular lipids isolated from exponentially growing cultures of S. cerevisiae, C. albicans and C. neoformans. Cells were incubated with the indicated [$^3$H]fatty acid (specific activity = 30 Ci/mmol, 100 µCi/ml media) for 1 h at 30° C. After the organisms were pelleted and washed, spheroplasts were prepared and total lipids extracted. Tests were done on two separate occasions. The incorporation of label from each of the oxatetradecanoic acid analogs and from palmitate into total cellular lipids is expressed as a percentage of the total amount of label incorporated from [$^3$H]myristate.

The following detailed Examples will further illustrate the invention although it will be understood that the invention is not limited to these Examples or the details described therein.

EXAMPLES

Synthesis of unlabeled fatty acid analogs

General procedures—Melting points were measured on a Laboratory Devices MEL-TEMP apparatus, in open capillaries and are uncorrected. $^1$H-NMR spectra were recorded on a Hitachi Perkin-Elmer R-600 high resolution NMR spectrometer or on a Varian VXR 400 superconducting NMR with Sun 5200 workstation in CDCl$_3$ and reported in ppm ($\delta$) downfield from Internal Me$_4$Si. IR spectra were recorded on a Perkin-Elmer 599 infrared spectrophotometer or on a Perkin-Elmer 298 infrared spectrophotometer. UV spectra were recorded on Perkin-Elmer Lambda 9 UV-VIS-NIR spectrophotometer. TLC analyses were performed on silica gel 60F-254 plates (layer thickness=0.2 mm). Column chromatography was carried out with Merck Kieselgel 60 (70-230 mesh). Combustion analyses were conducted by Atlantic Microlab Inc. (Atlanta, Ga.).

Oxatetradecanoic acids—3-Oxa-, 4-oxa-, 5-oxa-, 6-oxa-, 7-oxa-, 8-oxa-, 9-oxa-, 10-oxa-, 11-oxa-, 12-oxa-, and 13-oxatetradecanoic acids were synthesized and characterized exactly as described in Kishore et al., *J. Biol. Chem.* 266, 8835-8853 (1991).

4-Oxatridecanoic acid (O4, C13)—A mixture containing nonane-1-ol (1.0 g, 6.9 mmol), t-butylacrylate (1.75 g, 13.65 mmol) and tetrabutylammoniumhydrogen sulphate (0.5 g, 1.5 mmol) in 50% sodium hydroxide (2.8 mL) and toluene (3.0 mL) was heated at 70° C. with vigorous stirring for 2.5 h under an atmosphere of nitrogen. The reaction mixture was diluted with cold water (25 mL) and extracted with ethylacetate (3×15 mL). The organic phase was washed with saturated saline, dried (Na$_2$SO$_4$) and concentrated under reduced pressure. The resulting residue was tritutrated with cold ethylacetate, filtered and dried to give sodium salt of 4-oxatridecanoate (0.93 g, 56%) as a white powder. The free acid was obtained by acidification of the sodium salt followed by extraction with dichloromethane and concentration to give a colorless syrup: FTIR 3100, 2920, 2860, 1710 and 1120 cm$^{-1}$. $^1$H NMR (CDCl$_3$) $\delta$ 0.88 (t, 3H, J=7.2 Hz), 1.27 (m, 14 H), 1.57 (m, 2H), 2.63 (t, 2H, J=6.3 Hz), 3.46 (t, 2H, J=6.6 Hz), 3.7 (t, 2H, J=6.3 Hz); FAB MS m/z 229 (M-H+2 Li); HRMS calcd. for C$_{12}$H$_{23}$O$_3$Li$_2$ (M-H+2 Li) 229.1967; found 229.1962.

5-Oxatridecanoic acid (O5, C13)—n-Octanol [CH$_3$(CH$_2$)$_7$OH, 8.0 g, 61.43 mmol] and 4-bromobutyronitrile [Br(CH$_2$)$_3$CN, 9.09 g, 61.43 mmol] were added to a solution of NaOH (50% aqueous, 50 mL), benzene (50 mL) and Bu$_4$NHSO$_4$ (2.61 g, 7.68 mmol). The mixture was stirred for 3 days at room temp. Water (50 mL) was added and then the mixture was extracted with ethyl acetate (4×60 mL), washed with water (2×40 mL) dried over Na$_2$SO$_4$ and distilled (Kugelrohr) to yield 5-oxatridecanonitrile (1.90 g, 16%) as a colorless oil that was used directly in the subsequent reaction.

A solution of 5-oxatridecanonitrile (1.90 g, 9.6 mmol) in a mixture of acetic acid (10 mL) and concentrated HCl (50 mL) was refluxed for 20 h. After evaporation of the solvent in vacuo, water (50 mL) and ethyl acetate (100 mL) were added to the residue. The organic phase was washed with water (2×50 mL), brine (1×50 mL), and then dried over Na$_2$SO$_4$. After distillation (Kugelrohr device, 120°-125° C./0.1 torr) and column chromatography (silica gel) using ethyl acetate:hexane (1:1) as eluent, 5-Oxatridecanoic acid (0.66 g, 32%) was isolated as a colorless oil. IR: 3550-2300, 1700 cm$^{-1}$, $^1$H-NMR: 0.78-0.98 (t, 3H), 1.00-1.40 (m, 10H), 1.42-1.62 (p, 2H), 1.82-1.94 (p, 2H), 2.40-2.56 (t, 2H), 3.38-3.52 (m, 4H). Anal. Calcd. for C$_{12}$H$_{24}$O$_3$: C, 66.63, H, 11.18%; Found: C, 66.53, H, 11.14%.

5,13-dioxatetradecanoic acid (O5, O13)—7-Methoxyheptanol. Sodium hydride (60% in oil, 3.17 g, 79.1 mmol) was slurried in THF (100 mL), heptane-1,7 diol [HO(CH$_2$)$_7$OH, 950 g, 7.19 mmol] was added, and the mixture refluxed for 1 h. A solution of methyl iodide [CH$_3$I, 11.23 g, 79.1 mmol] in THF (50 mL) was added at once at room temperature and stirring continued for 72 h. Water (80 mL) was added and the mixture was extracted with ethyl acetate (4×60 mL), the organic phase was washed with water (2×50 mL), dried over anhydrous Na$_2$SO$_4$, and chromatographed (silica gel) using ethyl acetate:hexane (1:1) as eluent. After removal of solvent in vacuo, 7-methoxyheptanol was isolated (42%) as a colorless oil which was used directly in the next step.

5,13-Dioxatetradenonitrile—To a solution of 7-methoxyheptanol (7.70 g, 52.7 mmol) and 4-bromobutyronitrile [Br(CH$_2$)$_3$CN, 7.79 g, 52.7 mmol] was added 50% aqueous NaOH (50 mL), benzene (50 mL), and Bu$_4$NHSO$_4$ (2.23 g, 6.6 mmol). The reaction mixture was stirred at room temperature for 3 days. Extractive workup afforded the nitrile (4.40 g, 39%) as a yellow oil that was used directly in the next step.

5,13-Dioxatetradecanoic acid—To a solution of the nitrile (see above, 4.40 g, 20.6 mmol) was added NaOH pellets (4.10 g, 103.1 mmol), absolute ethanol (80 mL) and H$_2$O (60 mL). The reaction mixture was stirred at reflux for 16 h. Extractive workup followed by Kugelrohr distillation gave 5,13-dioxatetradecanoic acid (1.10 g, 23%) as a colorless oil, bp 150°-155° C./0.5 torr, IR 3600-2300, 1700 cm$^{-1}$, $^1$H-NMR: 1.20-1.50 (s, 6H), 1.50-1.68 (s, 4H), 1.82-2.00 (p, 2H), 2.40-2.53 (m, 2H), 3.21-3.62 (m, 9H). Anal. Calcd. for C$_{12}$H$_{24}$O$_4$: C, 62.04, H, 10.41%; Found: C, 62.11, H, 10.39%.

4,13-Dioxztetradecanoic acid (O4, O13)—

8-Methoxyoctanol, prepared by the method described for 7-methoxyheptanol (see above), was isolated (42%) as yellow oil and used without further purification.

4,13-Dioxatetradecanonitrile, prepared as described above, was isolated (74%) as a colorless liquid, and used without purification.

4,13-Dioxatetradecanoic acid was obtained (22%) as described above as a pale yellow oil. IR: 3700-2300, 1720 cm$^{-1}$. $^1$HNMR: 1.20-1.42 (s, 8H), 1.43-1.65 (p, 4H), 2.58-2.64 (t, 2H), 3.23-3.58 (m, 7H), 3.62-3.73 (t, 2H). Anal. Calcd. for C$_{12}$H$_{24}$O$_4$: C, 62.04, H, 10.41%; Found: C, 61.86, H, 10.42%.

Synthesis of labeled fatty acid analogs

Tritated 6-oxa-, 11-oxa, and 13-oxatetradecanoic acids—The methods used to synthesize and purify [9,10(n)$^3$H]6-oxatetradecanoate (105 Ci/mmol), [9,10(n)$^3$H]11-oxatetradecanoate (31.7 Ci/mmol), and [10,11(n)$^3$H]13-oxatetradecanoate (137 Ci/mmol) have been described in previous publications [Devadas et al., *J. Labelled Comp. Radiooharmaceut.* 29, 157-164 (1991); Heuckeroth and Gordon, *Proc. Natl. Acad. Sci. USA* 86, 5262-5266 (1989)].

[6,7(n)$^3$H]-4-oxatetradecanoic acid t-Butyl-3-(2-decynloxy)propionate—A mixture of 2-decyn-1-ol(0.35 g, 2.3 mmol), t-butyl acrylate (0.35 g, 2.73 mmol) in 50% sodium hydroxide (3 mL) and toluene (3 mL) was heated at 65 C under an atmosphere of argon with vigorous stirring. After 2 h, the reaction mixture was poured into water (10 mL) containing crushed ice and extracted with EtOAc (3×10 mL). The EtOAc extract was washed first with cold 2N HCl (10 mL) followed by water (3×10 mL), dried (Na$_2$SO$_4$) and concentrated under reduced pressure. The residue thus obtained was purified by flash chromatography using 4% EtOAc in hexane to furnish 1 (0.32 g, 50%) as a colorless oil: FT IR 2940, 2860, 2230, 1730, 1370, 1160, 1100 cm$^{-1}$; $^1$H NMR (CDCl$_3$) δ 0.88 (t, 3H), 1.2–1.5 (m, 10H), 1.45 (s, 9H), 2.2 (m, 2H), 2.54 (t, 2H), 3.73 (t, 2H), 4.14 (m, 2H); FAB MS m/z 289 (M+Li); HRMS Calcd. for C$_{17}$H$_{30}$O$_3$Li(M+Li): 289.25; found: 289.23.

3-(2-Deoynloxy)propionic acid—A solution of t-butyl-3-(2-decynloxy)propionate (0.32 g, 1.13 mmol) in acetonitrile (5 mL) containing p-toluenesulfonic acid (0.05 g, 0.26 mmol) was heated at 70° C. under argon atmosphere for 2 h. The reaction mixture was concentrated under reduced pressure and the residue was purified by flash chromatography using 25% EtOAc in hexane to give 3-(2-decynloxy)propionic acid (0.16 g, 63%) as a colorless syrup: FT IR 2930, 2860, 2230, 1720, 1360, 1120, and 1100 cm$^{-1}$; $^1$H NMR (CDCl$_3$) δ0.88 (t, 3H), 1.27–1.3 (m, 10H), 2.2 (m, 2H), 2.66 (t, 2H, J=6.0 Hz), 3.8 (t, 2H, J=6.0 Hz), 4.18 (m, 2H); $^{13}$C NMR (CDCl$_3$) δ 3.88, 18.56, 22.43, 28.40, 28.60, 28.65, 31.54, 34.57, 8.68, 64.42, 75.20, 87.33, 177.46; FAB MX m/Z 233 (M+Li); HRMS: Calcd. for C$_{13}$H$_{22}$O$_3$Li(M+Li) 233.17; found: 233.17.

[6,7(n)$^3$H]-4-oxatetradecanoic acid 3-(2-Decynloxy)propionic acid (45 mg) dissolved in benzene (3 mL) was subjected to catalytic reduction using 10% Pd/C(10 mg) and tritium gas (25 Ci) at room temperature for 1 h. The catalyst was removed by filtration, the filtrate was concentrated under reduced pressure and the residue was purified by HPLC using a Techsphere 5μ ODS column (solvent A=methanol:dioxan:0.04M triethylamine formate (65:2:33), solvent B=methanol:dioxan:0.04M triethylamine formate (90:2:8), gradient=0–100% B developed over 15 min at a flow rate of 1 ml/min). This procedure yielded tritiated 4-oxatetradecanoic acid labeled at positions 6 and 7, with specific activity of 91 Ci/mmol and 98% radiochemical purity. The molecular weight (236) of the tritiated sample as determined by mass spectrometry was consistent with the structure.

Treatment of exponentially growing cultures of S. cerevisiae, C. albicans and C. neoformans with oxatetradecanoic acids and oxatrdecanoic acids—

Saccharomyces cerevisiae strain YM2061 (MATa ura3-52 his3Δ200 ade2-101 lys2-801 met LEU2::pRY181 can1; Flick and Johnston, Mol. Cell. Biol. 10, 4757–4769 (1990), Candida albicans strain B311 (obtained from the American Type Tissue Culture, Rockville, Md.), or Cryptococcus neoformans strain L210425 (a clinical isolate that is part of the permanent culture collection of the Mycology Laboratory, Barnes Hospital, St. Louis, Mo.) were grown overnight at 30 C. The S. cerevisiae strain was incubated in YPD medium (1% bacto-yeast extract, Gibco, Long Island, N.Y.), 2% bacto-peptone (Gibco), 2% dextrose). The C. albicans and C. neoformans strains were grown in Sabouraud's media (SAB; 2% (w/v) dextrose, 1% bacto-peptone). The following morning the cultures were diluted into fresh medium to the desired density at 600 nm (early log phase), and subsequently incubated in a rotary shaker at 30° C. until an A$_{600}$=0.5 (mid log phase) was achieved. The culture was then divided into 10 ml aliquots. A single 10 μl aliquot of a stock solution of fatty acid analog (prepared in various concentrations using absolute ethanol) was added to the culture so that the final concentration of the compound was 100–500 μM (T=0). Ten microliters of ethanol alone was added to one 10 ml culture which served as the negative control. Amphotericin B (AmB; in the form of Fungizone, Squibb) was added (final concentration=55 μM) to another culture which served as the positive control. At T=0 and 0.5–24 h after addition of fatty acid analog to the subcultures, an aliquot was removed for determining the density of the subculture at 600 nm. Cell viability was determined at each of these time points by (i) serially diluting the aliquot in 0.15M NaCl and counting cell number in a hemocytometer and (ii) plating 2–3 of the dilutions in triplicate onto plates of SAB/agar (C. albicans and C. neoformans) or YPD/agar (S. cerevisiae). These plates were subsequently incubated at 30° C. for 24–48 hr to allow for the growth of colonies. The data were expressed as the ratio of viable cells/ml in the fatty acid analog treated subculture to the number of viable cells/ml in the negative (ethanol) control culture.

Metabolic Labelling Tests

Analysis of the incorporation of exogenous fatty acids into cellular proteins—Cultures of S. cerevisiae YM2061, C. albicans B311, and C. neoformans L210425 were grown overnight at 30° C. in YPD or SAB broth. In the morning, C. albicans and C. neoformans were diluted to an A$_{600}$=0.6. All cultures were subsequently shaken at 30° C. until they achieved an A$_{600}$=1.2. A 5 ml aliquot of each culture was then incubated at 30° C. with 100 μCi/ml of either [9,10(n)$^3$H]myristate (NEN Research Products, Dupont, Boston, Mass.); [6,7(n)$^3$H]4-oxatetradecanoate; [9,10(n)$^3$H]6-oxatetradecanoate; [9,10(n)$^3$H]11-oxatetradecanoate; or [10,11(n)$^3$H]13-oxatetradecanoate (the final specific activity of all tritiated fatty acids=30 Ci/mmol, their final concentration=3.3 μM). The cultures were then chilled on ice for 5 min and the cells harvested by centrifugation at 4000×g for 5 min. The pellet was washed by gentle vortexing in 1 ml of phosphate buffered saline (PBS, maintained at 4° C.). The yeast cells were then pelleted by centrifugation (as above) and broken open by vortexing with 500 μm glass beads in a 200 μl solution containing 240 mM Tris-HCl, pH 6.8, 2% SDS, 0.4% β-mercaptoethanol, 0.002% bromophenol blue, and 10% glycerol. The solution was then boiled for 5 min and cellular debris was removed by centrifugation at 12,000×g for 10 min. One hundred μg [Lowry et al., J. Biol. Chem. 193, 265–275 (1951)] of lysate protein from each sample was subjected to denaturation, reduction and electrophoresis through 12% polyacrylamide gels containing 0.1% SDS [Laemmli, Nature 227, 680–685 (1970)]. Duplicate gels were incubated overnight with 1M Tris, pH 7.4, or 1N hydroxylamine, pH 10. Fluorography was performed by treating gels with EN$^3$HANCE (NEN Research Products, Dupont) and, following drying, exposing them to Kodak XAR film at −80° C.

Analysis of the incorporation of exogenous fatty acids into cellular phospholipids and neutral lipids— Five ml cultures were labeled with each of the 5 tritiated fatty acids or with [9,10(n)$^3$H]palmitate (30 Ci/mmol) at 30° C. for 60 min (S. cerevisiae and C. albicans) or for 75 min (C. neoformans) as described in the preceding paragraph. S. cerevisiae and C. albicans cells were then pelleted by centrifugation at 4000×g for 5 min. and washed first in water followed by a wash with 1M sorbitol. The yeast were subsequently resuspended in SCE buffer (1M sorbitol, 0.1M trisodium citrate, pH 5.8, 10 mM EDTA, pH 8.0) containing 250 mM dithiotreitol (DTT) and 10 mg/ml of *Arthobacter luteus* lyticase (Sigma Chemical Company, St. Louis; specific activity=200 units/mg). *C. neoformans* were also collected by centrifugation but were resuspended in 5 ml TED buffer (100 mM Tris-HCl, pH 8.0, 5 mM EDTA, 5mM β-mercaptoethanol). Cells were shaken at 30° C for 15 min, spun at 2000×g for 10 min., washed in a solution containing 20 mM 2-[N-morpholino]ethanesulfonic acid (MES), pH 6.0, and 1M sorbitol and then resuspended in 5 ml of solution containing 1M sorbitol, 0.035% β-mercaptoethanol and a lysing enzyme preparation from *Trichoderma harzianum* (Novozyme, Novo Biolabs, Danbury, Conn.; final concentration=2 mg/ml). After a 20-30 min incubation at 30° C. ~85% of the cells were converted to spheroplasts. Cellular lipids were then extracted from the spheroplasts using the method of Bligh and Dyer, *Can. J. Biochem. Physiol.* 37, 911-917 (1959), dried to completeness under a stream of nitrogen and stored at −20° C.

Dried lipids were resuspended in 500 μl CHCl$_3$:MeOH(1:1). A 2 μl aliquot was counted in a scintillation counter to determine the extent of incorporation of label into cellular lipids. Radiolabeled lipids (500,000 dpm) were spotted on the preconcentrating zone of Silica Gel 60 high performance thin layer chromatography (HPTLC) plates (Merck) adjacent to known lipid standards (obtained from Sigma). Phospholipids were separated in a single dimension using methyl acetate:2-propanol:chloroform:methanol:0.25% aq. KCl (25:25:28:10:7) [Heape et al., *J. Chromatogr.* 322, 391-395 (1985)]. Neutral lipids were separated using a hexane:anhydrous diethyl ether:acetic acid (90:10:1) solvent system [a modification of the separation scheme of Mangold and Malins, *J. Am. Oil Chem. Soc.* 37, 383-386 (1960)]. Solvent was run to the top of the plate and standards were visualized by iodine vapor. Radiolabeled lipids were identified by spraying the plate with EN$^3$HANCE (NEN Research Products, Dupont) and exposing it to Kodak XAR film at −80° C.

In vitro discontinuous NMT assay—This assay was carried out by conventional procedures as described by Duronio et al., *Methods: A Companion to Methods in Enzymol.* 1, 253-263 (1990); Kishore et al., *J. Biol. Chem.* 266, 8835-8853 (1991). Briefly, a single point assay was performed by first converting myristic acid or a fatty acid analog (final concentration=40 μM) to its CoA thioester using *Pseudomonas* acylCoA synthetase (EC 6.2.1.3, Sigma Chemical Co.). Following a 25 min incubation at 30° C., purified *E. coli* derived *S. cerevisiae* or *C. albicans* NMT [Rudnick et al., *Ibid.* 265, 13370-13378 (1990); Wiegand et al., *J. Biol. Chem.* 267, 8591-8598 (1992)], final concentration=0.1 μg/ml, was added to the reaction mixture together with a tritiated peptide substrate derived from residues 2-9 of the HIV-1 Pr55$^{gag}$(Gly-Ala-Arg-[$^3$H]Ala-Ser-Val-Leu-Ser-NH$_2$) [Kishore et al., supra (1991); specific activity=1.2 Ci/mmol; final concentration=23 μM]. After an additional 10 min incubation at 30° C., the enzymatically generated, radiolabeled acylpeptide was purified by reverse phase HPLC and quantitated using an in-line scintillation counter [Kishore et al., supra, (1991)]. The amount of analogpeptide formed was expressed as a percentage of the amount of myristoylpeptide formed in a parallel reference assay. All assays were performed in duplicate or triplicate.

Results

Surveys of the anti-fungal activities of tetradecanoic and tridecanoic acids with oxygen for methylene substitutions—A panel of myristic analogs in which each methylene from position 3 to 13 (C1=carboxyl) was replaced by oxygen were synthesized as described by Heuckeroth et al., *J. Biol. Chem.* 85. 8795-8799 (1988); Kishore et al., *Ibid* 266. 8835-8853 (1991). There are several consequences of substituting an oxygen for a methylene: (i) C—O bond lengths are shorter than C—C (1.41 Å compared to 1.54 Å); (ii) the bond angles are altered (C—C—C=109° versus 111° for C—O—C): (iii) since the hydrogen bonds of methylene are replaced by electron pairs, C—H bond interactions that influence hydrocarbon conformation are reduced; and (iv) the polarity is significantly affected [oxatetradecanoic acids have hydrophobicities equivalent to those of C10:0-C12:0 fatty acids in octanol/water partitioning assays, Heuckeroth et al., supra (1988)].

FIG. 1A shows the effect of adding a single 300 μM dose of one of several oxatetradecanoic acids to cultures of *C. neoformans* during the exponential phase growth at 30° C. (when the doubling time is ~2 h). A culture treated with ethanol (0.1%) was used as a negative control for two reasons: (i) each oxatetradecanoic acid was dissolved in absolute ethanol and this was the final concentraton of solvent in all analog-treated cultures; and (ii) preliminary tests had shown that 0.1% ethanol had no effect on growth when compared to a culture that received no additions. The myristic acid analogs tested produced a wide range of effects on the growth, as determined by optical density. 11-Oxatetradecanoic acid (O11) had virtually no effect on growth, whereas 300 μM 4-oxatetradecanoic acid (O4) produced a degree of growth arrest equivalent to that observed with 55 μM amphotericin B. O3 and O6 resulted in intermediate degrees of growth retardation. The fact that the A$_{600}$ remained constant for 24 h after addition of 300 μM O4 suggested that it was not producing cell lysis. Light microscopic examination of aliquots of the cultures taken 2 h after addition of analogs or ethanol failed to show any gross differences in cellular morphology.

FIG. 1B shows that 4 of the 10 oxatetradecanoic acids tested were fungicidal for *C. neoformans* at 300 μM. Their order of potency was O4>O5>O3~O6. In four independent tests, a single dose of O4 produced an average 10,000-fold decrease in viable cells within 1h after its addition to the culture. Further, modest (<1 log) reductions in viable cell number were noted between 1 and 7 h after treatment. Movement of the oxygen one position towards carboxyl or one position towards the ω terminus dramatically affected the fungicidal effect: 5-oxatetradecanoic acid (O5) reduced cell viability by 1000-fold whereas 3-oxatetradecanoic acid produced "only" a 10-fold reduction. As with O4, each of these other analogs suppressed growth over at least a 7 h period. 6-Oxatetradecanoic acid ultimately produced the same degree of reduction in cell viability as 3-oxatetradecanoic acid but the time course of its effect was initially slower, requiring 4 h to produce a 10-fold decrease in the number of viable cells (FIG. 1B). O7, O8, O10, O11, O12 and O13 had no measurable effect on the growth of *C. neoformans* at the concentration used for this screening assay, i.e. they were neither fungicidal nor fungistatic. Substitution of oxygen for methylene at C4 or C5 of 13-oxatetradecanoic acid (yielding 4,13 dioxa- and 5,13 dioxatetradecanoic acids, respectively) did not convert O13 to an active analog (FIG. 1B).

Shortening 4-oxa and 5-oxatetradecanoic acids by one methylene to 4-oxa- and 5-oxatridecanoic acid attenuated fungicidal activity 10 fold: 4-oxatridecanoic acid produced a 1000 fold reduction in viable cell number although its effect on viability required a longer period of time (6–7 hrs) to be fully demonstrated. 5-oxatridecanoic acid was not active at 300 μM (FIG. 1B).

FIG. 1C provides information about the fungicidal activity of 4-oxatetradecanoic acid at four different doses (100–300 μM). With increasing dose a progressive reduction of viable cell number is seen without an apparent change in the rate of killing. Amphotericin B (AmB, 55 μM) produced a $10^6$ fold reduction in viable cell number compared to the 10,000 fold reduction seen with 300 μM 4-oxatetradecanoic acid.

A gradual increase in cell number occurred between 8 and 24 hr after administration of the single dose of O4 (FIG. 1B and 1C). A series of tests were conducted to assess the metabolic stability of the compound (FIG. 2). Media was harvested from cells treated with a single dose of 300 μM O4 for 2 hr or for 24 hr and added to a exponentially growing culture of C. neoformans that had never been exposed to fatty acid analog. 100 fold and 10 fold decreases (respectively) in viable cell number were observed over the ensuing 2 hr (O4B and O4D in FIG. 2). This suggested that biologically active material was still present in the media even after it had been incubated with cells at 30° C. for up to 24 hr. When fresh media containing 300 μM 4-oxatetradecanoic acid was added to cells that had been exposed to fatty acid analog for 2 hr or for 24 hr, a further 5 fold reduction in viable cell number was observed (O4C and O4E, respectively in FIG. 2) indicating that these cells are still susceptible to the compound or a metabolite. Exponentially growing cultures were also exposed to a single 300 μM dose of O4, a single dose of 0.1% EtOH, or to no additions. Aliquots of each of the cultures were removed 4 and 24 hr later and plated on Sabouraud/agar. Single colonies were picked from these plates, grown up in Sabouraud (SAB) media and at mid-log phase of growth exposed to a single dose of 300 μM O4. In all cases, an identical decrease in cell viability (magnitude and time course) was observed. Together these results suggest that the cells do not become resistant or tolerant to O4.

Figure 3A:
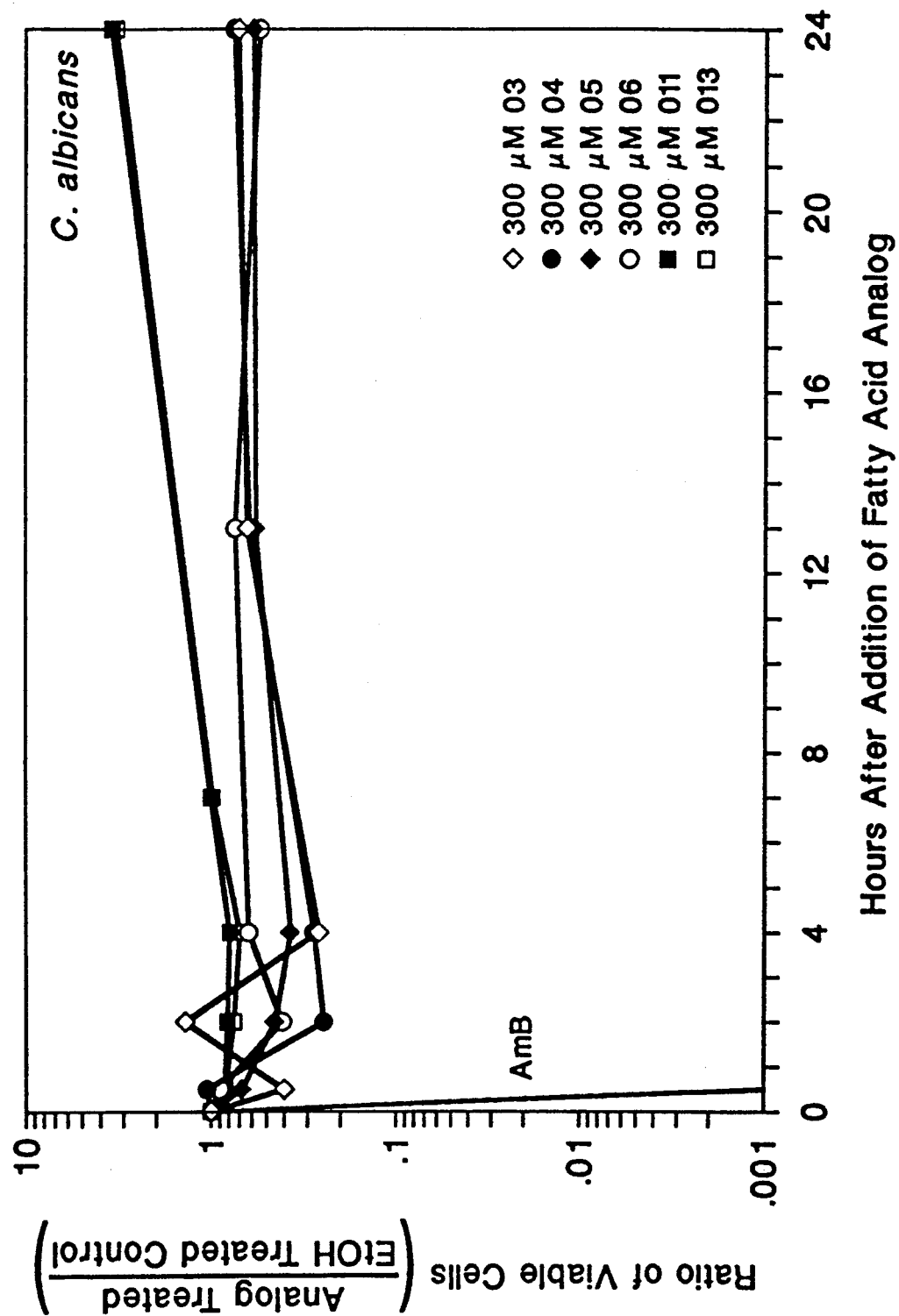
Figure 3B:
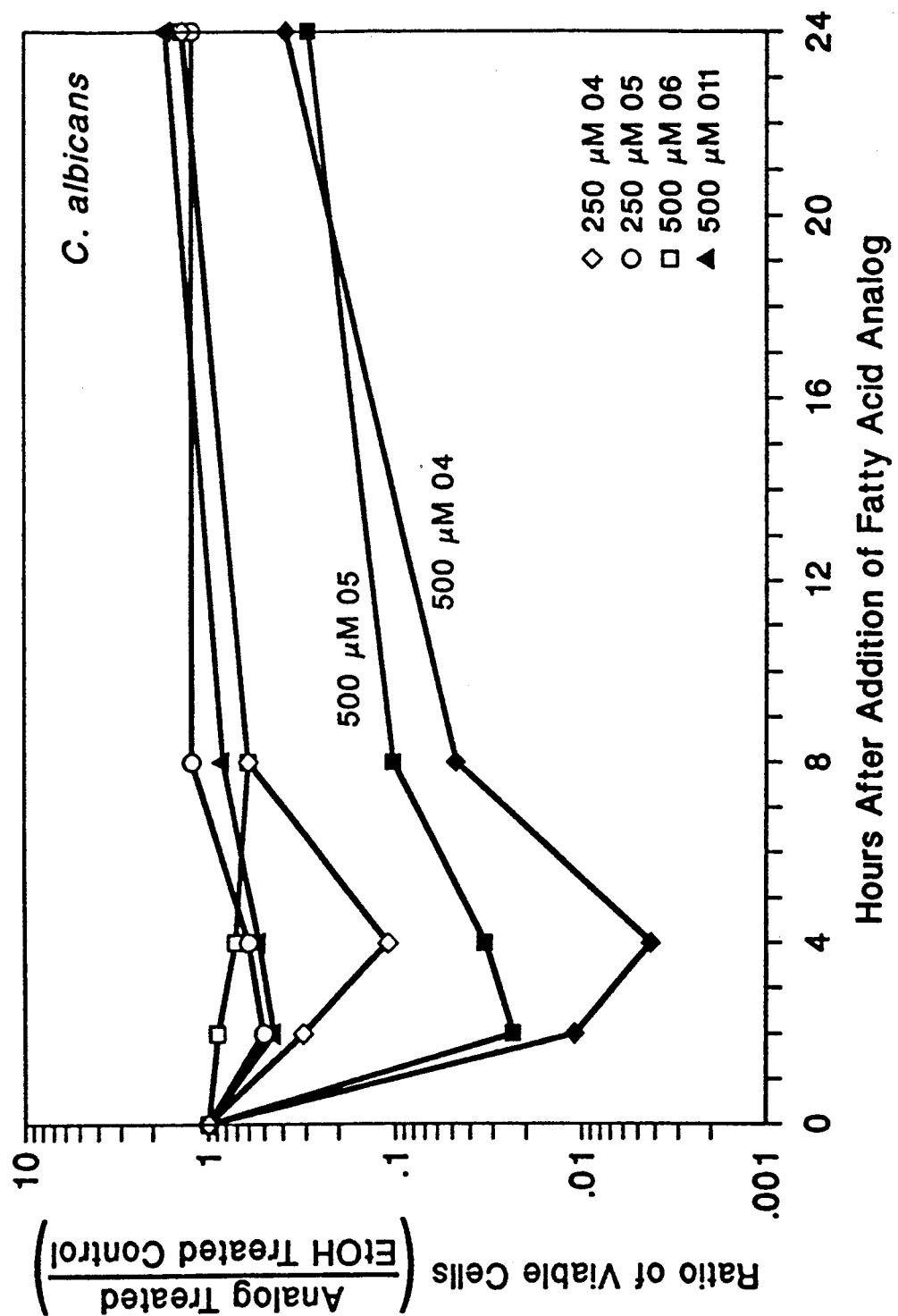
Figure 3C:
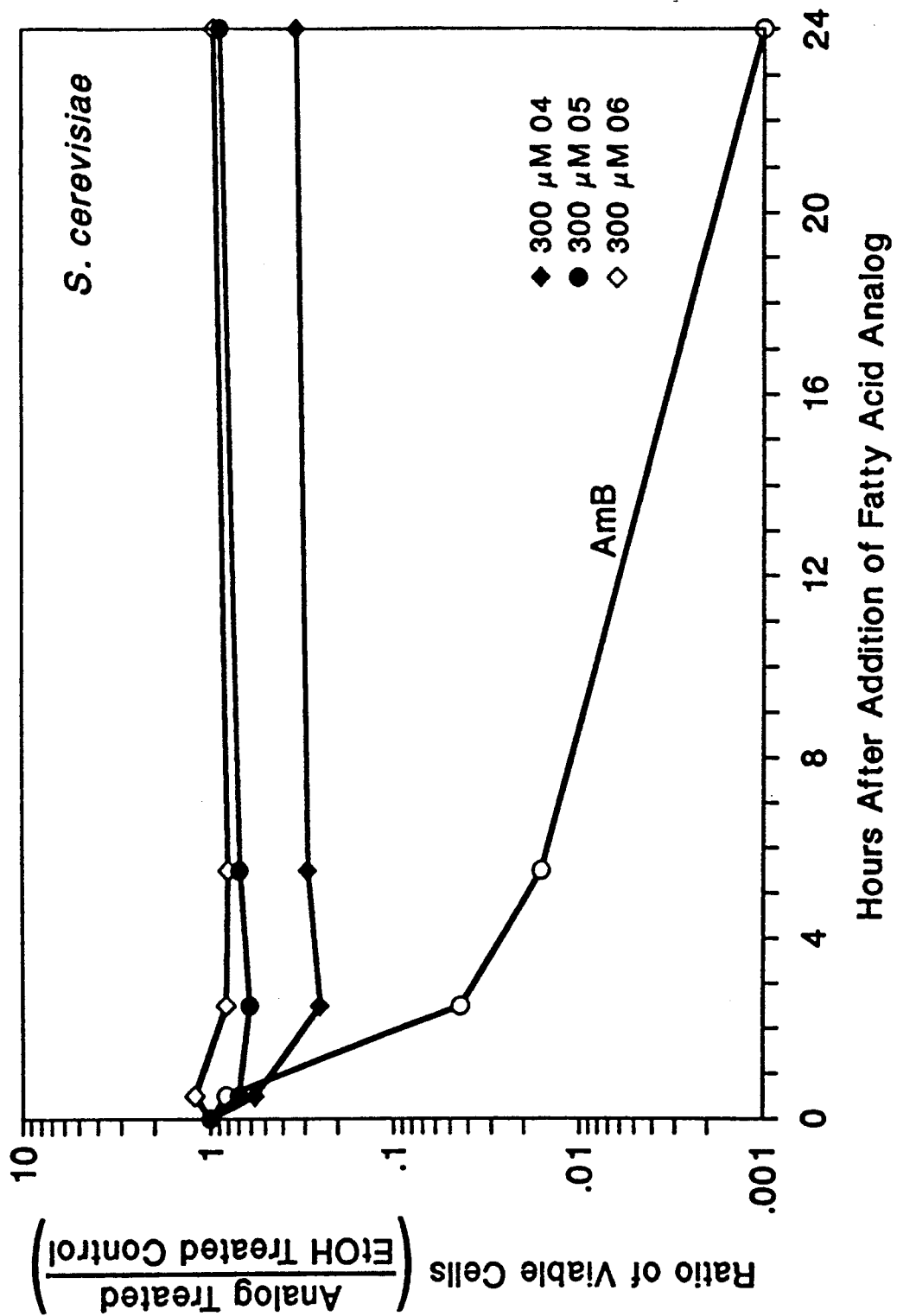
Figure 3D:
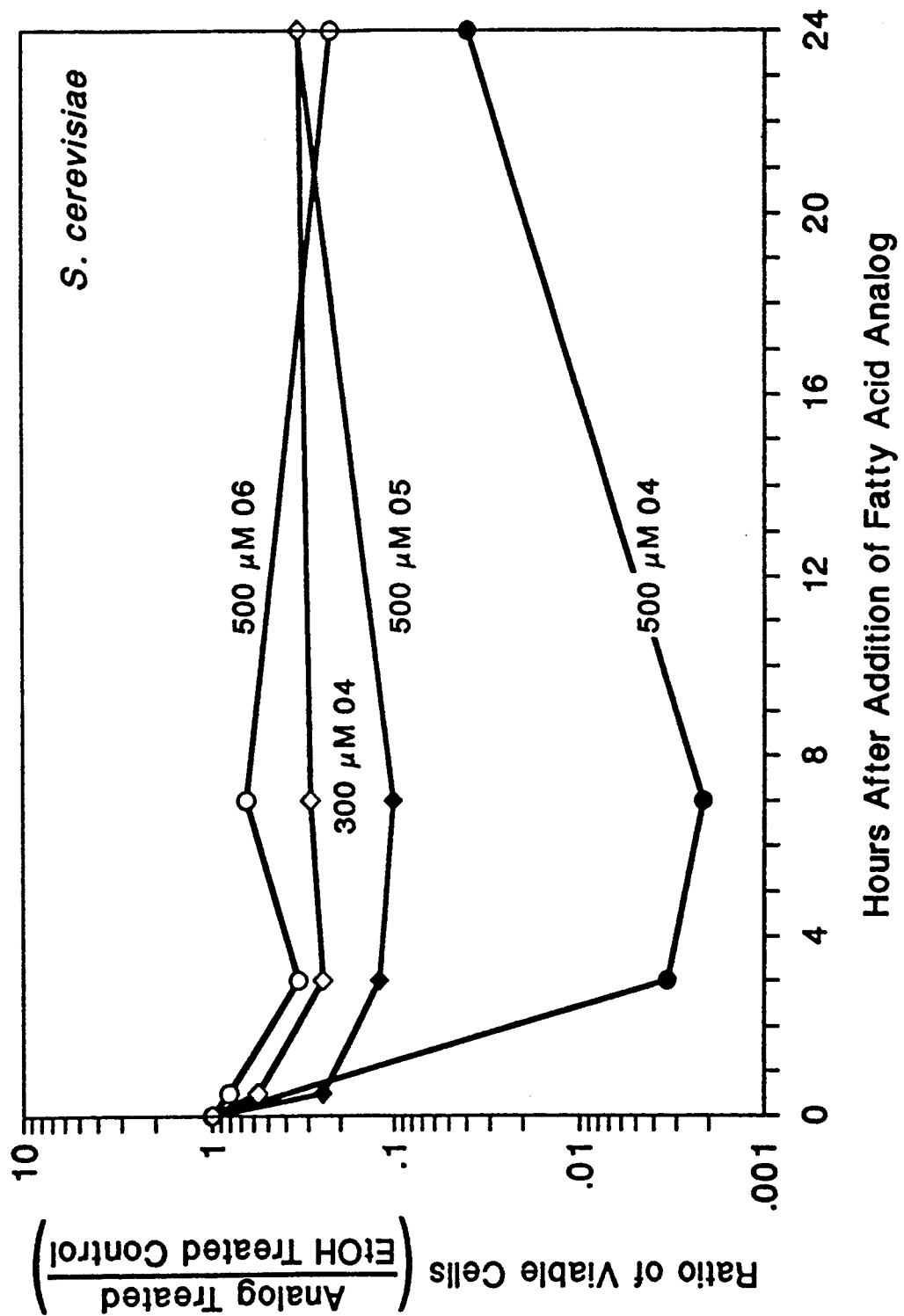

To assess the spectrum of anti-fungal activity of the oxatetradecanoic analogs, cultures of C. albicans and S. cerevisiae were treated during exponential growth at 30° C. with a single 300 μM dose of O3, O4, O5, O6, O11 or O13. 4-Oxa- and 5-oxatetradecanoic acids produced minimal (<5 fold) reductions in the number of viable S. cerevisiae or C. albicans 2 hr after their addition to the culture media (FIG. 3A, 3C). Increasing the dose to 500 μM resulted in a 10–100 fold reduction in the number of viable organisms with O4 exhibiting greater potency than O5 (FIG. 3B, 3D). None of the other fatty acid analogs had any effect on viable cell number at this concentration, underscoring the specificity of the response to O4 and O5.

In vitro studies of purified S. cerevisiae and C. albicans NMT reveal differences in the kinetic properties of oxatetradecanoic and oxatridecanoic acid analogs—To begin to understand the mechanism which underlies the fungicidal activities of some but not all of the oxygen containing fatty acid analogs, the relative activities of the sixteen oxatri-, oxatetradecanoic acids and dioxatetradecanoic acids were examined in an in vitro assay. The two step assay measures NMT-dependent transfer of the acyl chain from an enzymatically generated acyl-CoA to a radiolabeled peptide substrate. The nonspecific [Shimizu et al., Anal. Biochem. 107, 193–198 (1980); Kishore et al., supra (1991); Devadas et al., J. Biol. Chem. 267, 7224–7239 (1992)] Pseudomonas acylCoA synthetase was first incubated with an unlabeled analog or myristate. An octapeptide representing residues 2–9 of HIV-1 Pr55$^{gag}$ was then added together with purified S. cerevisiae [Rudnick et al, Ibid, 265, 13370–13378 (1990)] or C. albicans NMT [Wiegand et al., J. Biol. Chem. 267 8591–8598 (1992)]. The tritiated octapeptide was selected because it had been used extensively to characterize the acylCoA substrate specificity of purified E. coli derived S. cerevisiae NMT [Kishore et al., supra (1991); Devadas et al., supra (1992)]. Pseudomonas acylCoA synthetase is able to convert each of the oxatetradecanoic acids to their CoA thioesters with an efficiency similar to that obtained with myristate [range=50–70%; Kishore et al., supra (1991)]. Once converted to their acylCoAs, the oxatetradecanoic acids were as active as myristoyl CoA for both S. cerevisiae and C. albicans NMT (FIG. 4). Surprisingly, the activity of 4-oxatetradecanoylCoA was ~3 fold greater than myristoylCoA, 5-oxatetradecanoylCoA was 1.5 to 2 fold greater while 3-oxatetradecanoylCoA was equivalent to myristate. The two oxatridecanoylCoAs were poorer substrates than the corresponding oxatetradecanoylCoAs while the dioxatetradecanoylCoAs were the least active. The profile of relative analogCoA activity was similar for the two orthologous acyltransferases. However, in neither case could a simple correlation be made between activity of the analogCoA (in the presence of the HIV-1 Pr55$^{gag}$ octapeptide) and its ability to affect growth of the two yeasts (compare FIGS. 1, 3 and 4).

Metabolic labelling studies using tritiated oxatetradecanoic acids confirm that they are incorporated in cellular N-myristoylproteins—A series of metabolic labeling studies were performed to compare and contrast the spectrum of N-myristoylproteins made by S. cerevisiae, C. albicans and C. neoformans during exponential growth at 30° C. on rich medium and to define the patterns of incorporation of four tritiated oxatetradecanoic acids (including O4) into cellular N-myristoylproteins. The results are presented in FIG. 5.

The data presented in FIG. 5 indicate that C. neoformans, like S. cerevisiae and C. albicans, incorporates exogenous [$^3$H]myristate into cellular proteins via a linkage that is resistant to 1N hydroxylamine (pH 10). Incubation of these two fungal species with [$^3$H]palmitate for 1 hr failed to produce any labeled proteins with hydroxylamine resistant linkages. This observation suggested that the labeling of polypeptides observed after addition of [$^3$H]myristate to the medium does not represent the result of metabolic conversion of the fatty acid to [$^3$H]amino acids.

The protein species labeled most intensely in C. neoformans and C. albicans have masses of ~20 kDa (FIG. 5B, C). Moreover, the intensities of these bands appear to be comparable in the 3 organisms. Using these bands as internal standards, it appears that the number of N-myristoylproteins which accumulate to detectable levels in C. albicans and C. neoformans is considerably smaller than in S. cerevisiae.

Analog specific differences in the labeling of N-myristoylproteins by tritiated O4, O6, O11, and O13 were observed within and between organisms (FIG. 5). For example, exogenous O4 produced more intense labeling of *S. cerevisiae* and *C. albicans* N-myristoylproteins than did [³H]myristate while producing comparable labeling in *C. neoformans*. O6 produced more intense labeling of 20 and 16 kDa *C. neoformans* N-myristoylproteins than did myristate (FIG. 5C) yet it failed to label cellular N-myristoylproteins in *S. cerevisiae* (FIG. 5A) and barely labeled *C. albicans* N-myristoylproteins (FIG. 5B). The 16 kDa *C. neoformans* N-myristoylprotein was very poorly labeled compared to labeling of the 20 kDa protein (FIG. 5C). *S. cerevisiae* also provided a number of other examples of analog-specific incorporation (e.g. O4 is incorporated into the 55 kDa Gpal polypeptide but not O13) even though both fatty acids label the 20 kDa Arfs with comparable intensity: see FIG. 5A).

The metabolic labeling studies therefore confirm that O4 is a substrate for *S. cerevisiae, C. albicans* and *C. neoformans* acylCoA synthetases and NMTs and that it is incorporated into their cellular N-myristoylproteins with an efficiency comparable to or exceeding that of myristate. The data also indicate that the extent of incorporation of a given analog into cellular N-myristoylproteins cannot be simply correlated with its fungicidal activity: e.g. tritiated O6 labels *C. neoformans* N-myristoylproteins more efficiently than either O4 or myristate yet unexpectedly produces minimal reductions in viable cell number (compare FIG. 5C with FIG. 1B).

Metabolic labeling studies reveal analog-specific differences in incorporation into cellular phospholipids and neutral lipids—The antifungal activity of the oxatetradecanoic acid analogs may be due to their incorporation into cellular lipids and/or to their effects on the activities of enzymes that regulate synthesis and metabolic processing of phospholipids and neutral lipids. Little is known about regulation of lipid metabolism in *C. neoformans*. Detailed studies of *S. cerevisiae* [reviewed by Kent et al., *FASEB J* 5, 2258–2266 (1991)] and *C. albicans* [Mago and Khuller, *J. Gen. Microbiol,* 136, 993–996 (1990)] suggest that phospholipid biosynthesis occurs along pathways which are similar to those present in mammalian cells. Phosphatidylcholine, phosphatidylserine, phosphatidylinositol, and phosphatidylethanolamine are the major phospholipid classes in these organisms while phosphatidic acid and cardiolipin represent only minor components. The principal neutral lipids are triacylglycerol, free and esterified sterols, and free fatty acids [Kaneko, *Lipids* 11, 837–844 (1976); Henry et al., in *The Mol. Biol. of the Yeast Saccharomyces: Metabolism and Gene Expression* (Strathern, Jones and Broach, eds.), pp. 101–158, Cold Spring Harbor Lab., N.Y.]. Growth conditions, including temperature, can affect the composition of membrane lipids: for example, membrane lipids contain relatively longer and more saturated acyl chains when *S. cerevisiae* is grown at higher compared to lower temperatures. [Okuyama et al., *J. Biol. Chem.* 254, 12281–12284 (1979); Hori et al., *J. Biochem.* 101 101, 949–956 (1987); Low and Parks *Lipids* 22, 715–720 (1987).]

Exponentially growing cultures of *S. cerevisiae, C. albicans*, and *C. neoformans* were labeled with either tritiated myristate, 4-oxa-, 6-oxa-, 11-oxa-, and 13-oxatetradecanoic acids as well as palmitate for 1 hr at 30° C. The conditions used for labeling were identical to those used to study incorporation of exogenous fatty acids into cellular N-myristoylproteins. FIG. 6 documents the incorporation of label into total cellular lipids when the three organisms were incubated with each of the five fatty acid analogs. The extent of analog incorporation varied with different analogs within and between organisms. The label from O4 was incorporated into *C. albicans* and *C. neoformans* lipids to a greater extent than any of the other analogs (27–28% of the amount observed with [³H]myristate).

The antifungal agent described herein can be used for administration to mammalian hosts infected with *Cryptococcus neoformans* and the like by conventional means, preferably in formulations with pharmaceutically acceptable diluents and carriers. The amount of the active agent to be administered must be a fungicidally effective amount, that is, an amount which is medically beneficial but does not present toxic effects which overweigh the advantages which accompany its use. It would be expected that the daily adult human dosage would normally range upward from about one milligram of the active compound. A suitable route of administration is orally in the form of capsules, tablets, syrups, elixirs and the like, although parenteral administration also can be used. Appropriate formulations of the active compound in pharmaceutically acceptable diluents and carriers in therapeutic dosage form can be prepared by reference to general texts in the fields such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. All such other examples are included within the scope of the appended claims.

What is claimed is:

1. A method for controlling the growth of *Cryptococcus neoformans* comprising subjecting said *Cryptococcus neoformans* to a small but fungicidally effective amount of 4-oxatetradecanoic acid or a $C_1$-$C_4$ alkyl ester thereof.

2. The method of claim 1 in which a cell culture of said *Cryptococcus neoformans* is subjected to from about 100 to 300 µM concentration of 4-oxatetradecanoic acid.

* * * * *

UNITED STATES PATENT AND TRADEMARK OFFICE
CERTIFICATE OF CORRECTION

PATENT NO. : 5,236,955
DATED : AUG. 17, 1993
INVENTOR(S) : JEFFREY I. GORDON

It is certified that error appears in the above-identified patent and that said Letters Patent is hereby corrected as shown below:

In the title page, left-hand col. at [75] Inventors, the initial "T" should read --I--.
At col. 3, line 52, "Cultreus" should read --Cultures--.
At col. 4, line 10, "alphotericin" should read --amphotericin--.
At col. 4, lines 18-19, cancel --2-9 of HIV-tritiated octapeptide derived from residues--.
At col. 7, line 10, "Deovnloxy" should read --Decynloxy--.
At col. 7, line 54, "30 C" should read --30°C--.
At col. 12, line 25, "-3" should read -- ~ 3--.
At col. 12, line 60, "-20" should read -- ~ 20--.

Signed and Sealed this

Nineteenth Day of September, 1995

Attest:

BRUCE LEHMAN

*Attesting Officer*    *Commissioner of Patents and Trademarks*